(12) United States Patent
Montana et al.

(10) Patent No.: US 8,669,248 B1
(45) Date of Patent: Mar. 11, 2014

(54) ADENINE INHIBITORS OF HSP90

(76) Inventors: John Montana, Harlow (GB); Janusz Kulagowski, Harlow (GB); Hazel Hunt, Harlow (GB); Yukari Perrella, Brookline, MA (US)

( * ) Notice: Subject to any disclaimer, the term of this patent is extended or adjusted under 35 U.S.C. 154(b) by 150 days.

(21) Appl. No.: 13/249,914

(22) Filed: Sep. 30, 2011

Related U.S. Application Data

(60) Provisional application No. 61/388,123, filed on Sep. 30, 2010.

(51) Int. Cl.
*C07D 413/06* (2006.01)
*A61K 31/538* (2006.01)

(52) U.S. Cl.
USPC ........................................ 514/230.5; 544/105

(58) Field of Classification Search
USPC ........................................ 544/105; 514/230.5
See application file for complete search history.

(56) References Cited

PUBLICATIONS

Zhang et al. Journal of Medicinal Chemistry (2006), 49(17), 5352-5362.*

* cited by examiner

*Primary Examiner* — Kahsay Habte
(74) *Attorney, Agent, or Firm* — Clark+Elbing LLP

(57) ABSTRACT

In general, the present invention relates to small molecule inhibitors of the heat shock protein 90 family of chaperone proteins. The invention also features pharmaceutical compositions and kits that include the compounds and compositions of the invention. The invention further relates to the medical use of these compounds and compositions for the treatment of neurodegenerative diseases.

15 Claims, No Drawings

ADENINE INHIBITORS OF HSP90

CROSS REFERENCE TO RELATED APPLICATIONS

This application claims benefit of U.S. Provisional Application No. 61/388,123, filed Sep. 30, 2010, which is hereby incorporated by reference in its entirety.

BACKGROUND OF THE INVENTION

In general, the present invention relates to small molecule inhibitors of the heat shock protein 90 (Hsp90) family of chaperone proteins, and pharmaceutical compositions thereof. The invention also features pharmaceutical compositions and kits that include the compounds and compositions of the invention. The invention further relates to the medical use of these compounds and compositions for the treatment of neurodegenerative diseases.

Hsp90 proteins are implicated in stabilizing protein conformations, maintaining the function of many cell-signaling proteins, and ATPase activity. Hsp90 activity is also required for the proper folding, stabilization, activation, and localization of oncoproteins involved in tumor progression (Pearl et al., *Annu. Rev. Biochem.* 75:271-94, 2006, and Luo et al., *BMC Neuroscience* 9(Suppl 2):57, 2008). The N-terminus ATP binding domain is responsible for the ATPase activity of this protein: this adenine nucleotide binding pocket is highly conserved among all Hsp90 proteins from bacteria to mammals but is not present in other chaperones (Grenert et al., *J. Biol. Chem.* 272:23843-50, 1997).

Crystallographic studies have shown that several Hsp90 inhibitors, such as the antitumor antibiotic geldanamycin, occupy the N-terminus ATP binding site (Roe et al., *J. Med. Chem.* 42:260-266, 1999), resulting in inhibition of Hsp90 ATPase activity and function. The use and therapeutic efficacy of geldanamycin and other Hsp90 inhibitors as antitumor agents relates to blocking multiple signaling pathways (see, e.g., Workman et al., *Ann. N.Y. Acad. Sci.* 1113:202-16, 2007, Chiosis, *Expert Opin. Ther. Targets* 10:37-50, 2006, and Xu et al., *Clin. Cancer Res.* 13:1625-9, 2007) and the increased level of Hsp90 activity in many tumors (Kamal et al., *Nature* 425:40710, 2003, and Mosseret al., *Oncogene* 23:2907-2918, 2004).

Increased levels of Hsp90 have also been implicated in neurodegenerative disorders, including Alzheimer's, Parkinson's, and Huntington's disease, and tauopathies (Dou et al., *Proc. Natl. Acad. Sci. USA* 100:721-726, 2003, and Ardley et al., *Mol. Biol. Cell.* 14:4541-4556, 2003). Tauopathies are neurodegenerative diseases characterized by tau protein abnormalities, which then result in the accumulation of hyperphosphorylated and aggregated tau protein (Murray et al., *Biochem. Soc. Trans.* 33:595-599, 2005, and Kosik et al., *Biochim. Biophys. Acta.* 1739:298-310, 2005). It has been proposed that hyperphosphorylated tau in Alzheimer's disease is a pathogenic process caused by aberrant activation of kinases, particularly cdk5 and GSK 133 (Dermaut et al., *Trends Genet.* 21:664-672, 2005, and Lau et al., *Curr. Top. Med. Chem.* 4:395-415, 2002). Other studies have shown that Hsp90 stabilizes p35, an activator of cdk5, leading to increased tau phosphorylation (Luo et al., *Proc. Natl. Acad. Sci. USA* 104:9511-9516, 2007 and Dickey et al., *J. Clin. Invest.* 117:648-658, 2007). It has also been shown that Hsp90 inhibition activates heat shock factor 1 (HSF1), which in turn increases the expression of Hsp70 (Ciechanover et al., *Neuron* 40:427-410, 2003,). Increased Hsp70 promotes tau solubility and binding to microtubules, inhibits protein aggregation, and enhances degradation.

Accordingly, inhibitors of Hsp90 represent beneficial therapeutics for the treatment of disorders such as cancer, neurodegenerative diseases, or viral infection.

DETAILED DESCRIPTION OF THE INVENTION

In one aspect, the invention features a compound having a structure according to the following formula,

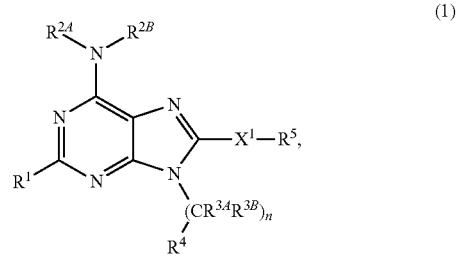

(1)

or a tautomer or pharmaceutically acceptable salt, solvate, or prodrug thereof, wherein
$R^1$ is H, halogen, CN, $C_{1-6}$alkoxy, $C_{1-6}$fluoroalkoxy, or $C_{1-6}$alkyl;
$R^{2A}$ and $R^{2B}$ are each H;
each $R^{3A}$ and $R^{3B}$ is, independently, H, halogen, or $C_{1-6}$alkyl;
n is 2, 3, or 4;
$R^4$ is H, $C_{3-9}$cycloalkyl, 3-9 membered heterocyclyl, or $NR^{4A}R^{4B}$;
$R^{4A}$ and $R^{4B}$ are each, independently, H or $C_{1-6}$alkyl;
$X^1$ is $CH_2$, S, or SO; and
$R^5$ is a bicyclic heteroaryl selected from Substructures A, B, C, and D
wherein
(a) Substructure A is selected from

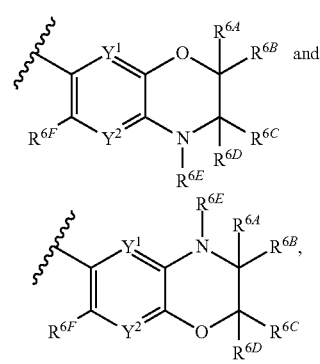

wherein
each of $R^{6A}$, $R^{6B}$, $R^{6C}$, and $R^{6D}$ is, independently, H or $C_{1-6}$alkyl, or $R^{6A}$ and $R^{6B}$, or $R^{6C}$ and $R^{6D}$, combine to form $=$O or $C_{3-9}$cycloalkyl,
$R^{6E}$ is H, $C_{1-6}$alkyl, or alk$C_{3-9}$cycloalkyl,
$R^{6F}$ is H, halogen, $C_{1-6}$alkyl, $C_{1-6}$haloalkyl, $C_{1-6}$alkoxy, $C_{1-6}$haloalkoxy, $C_{1-6}$alkylthio, $C_{1-6}$alkylsulfonyl, $C_{1-6}$alkylamino, or di($C_{1-6}$alkyl)amino;
$Y^1$ and $Y^2$ are, independently, N or $CR^{6G}$, and
$R^{6G}$ is H, H halogen, CN, $C_{1-6}$-alkyl, $C_{1-6}$haloalkyl, $C_{1-6}$-alkoxy, $C_{1-6}$haloalkoxy, hydroxy$C_{1-6}$ alkyl, or $C_{1-6}$ alkoxy-$C_{1-6}$ alkyl;

(b) Substructure B is selected from

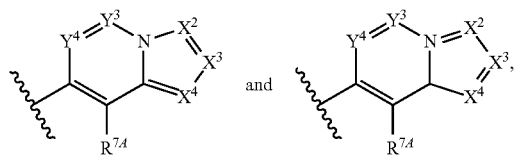

wherein
$R^{7A}$ is H, halogen, $C_{1-6}$alkyl, $C_{1-6}$haloalkyl, $C_{1-6}$alkoxy, $C_{1-6}$haloalkoxy, $C_{1-6}$alkylthio, $C_{1-6}$alkylsulfonyl, $C_{1-6}$alkylamino, or di($C_{1-6}$alkylamino, $Y^3$ and $Y^4$ are, independently, N or $CR^{7B}$, each $X^2$, $X^3$, and $X^4$ is, independently, N or $CR^{7C}$, each $R^{7B}$ and $R^{7C}$ is, independently, H, halogen, CN, $C_{1-6}$alkyl, $C_{1-6}$haloalkyl, $C_{1-6}$alkoxy, $C_{1-6}$haloalkoxy, hydroxy$C_{1-6}$ alkyl, or $C_{1-6}$alkoxy-$C_{1-6}$alkyl, and wherein no more than 4 of $Y^3$, $Y^4$, $X^2$, $X^3$, and $X^4$ are N;

(c) Substructure C is selected from

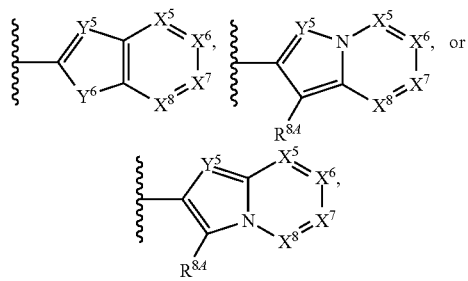

wherein $Y^5$ is N or $CR^{8B}$, $Y^6$ is $NR^{8C}$, O, or S, each $R^{8A}$ and $R^{8B}$ is, independently, H, halogen, CN, $C_{1-6}$alkyl, $C_{1-6}$haloalkyl, $C_{1-6}$alkoxy, $C_{1-6}$haloalkoxy, hydroxy$C_{1-6}$ alkyl, or $C_{1-6}$ alkoxy-$C_{1-6}$alkyl, each $R^{8C}$ is H, $C_{1-6}$alkyl, or alk $C_{3-9}$cycloalkyl, each $X^5$, $X^6$, $X^7$, and $X^8$ is, independently, N or $CR^{8D}$, and each $R^{8D}$ is, independently, H, halogen, CN, $C_{1-6}$alkyl, $C_{1-6}$haloalkyl, $C_{1-6}$alkoxy, $C_{1-6}$haloalkoxy, hydroxy$C_{1-6}$ alkyl, or $C_{1-6}$ alkoxy-$C_{1-6}$ alkyl; and wherein no more than two of $X^5$, $X^6$, $X^7$, and $X^8$ are N; and (d) Substructure D has the following structure,

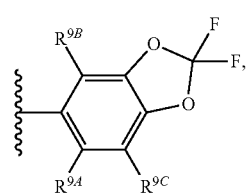

wherein $R^{9A}$, $R^{9B}$, and $R^{9C}$ are selected, independently, from H, halogen, CN, $C_{1-6}$alkyl, $C_{1-6}$haloalkyl, $C_{1-6}$alkoxy, $C_{1-6}$haloalkoxy, hydroxy$C_{1-6}$ alkyl, or $C_{1-6}$alkoxy-$C_{1-6}$alkyl; and wherein when $R^1$ is H, —$(CR^{3A}R^{3B})_nR^4$ is -nBu, and $X^1$ is S, $R^5$ is not benzothiazole, 5-chlorobenzothiazole, or 5-methoxybenzothiazole.

In certain embodiments, $R^1$ is H, Cl, F, $OCH_3$, $OCHF_2$, or $CH_3$. In other embodiments, $X^1$ is $CH_2$ or S.

In still other embodiments, when $R^5$ is Substructure A, $R^{6F}$ is H or halogen (e.g., iodine or bromine), each of $R^{6A}$, $R^{6B}$, $R^{6C}$, and $R^{6D}$ is H, $R^{6A}$ and $R^{6B}$ combine to form =O, $R^{6C}$ and $R^{6D}$ combine to form =O, and/or $R^{6E}$ is $C_{1-6}$ alkyl, with the proviso that, when $R^{6A}$ and $R^{6B}$ combine to form =O, $R^{6C}$ and $R^{6D}$ do not combine to form =O, and when $R^{6C}$ and $R^{6D}$ combine to form =O, $R^{6A}$ and $R^{6B}$ do not combine to form =O.

In yet other embodiments, when $R^5$ is Substructure B, $R^{7A}$ is H or halogen (e.g., iodine or bromine).

In other embodiments, $R^5$ is Substructure C and Substructure C is selected from the group consisting of

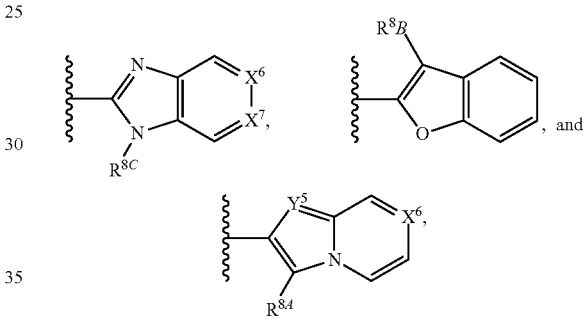

wherein $R^{8A}$, $R^{8B}$, and $R^{8C}$ are branched $C_{1-6}$ alkyl, $Y^5$ is N or CH, and $X^6$ and/or $X^7$ is N.

In any of the above embodiments, n is desirably 2 or 3, each $R^{3A}$ and $R^{3B}$ is H, and/or $R^4$ is $NR^{4A}R^{4B}$ (e.g., $R^{4a}$ is H and $R^{4B}$ is branched $C_{1-6}$ alkyl). For example, —$(CR^{3A}R^{3B})_nR^4$ can be —$(CH_2)_2NHCH_2CH(CH_3)_2$.

In certain embodiments, the compound is selected from the group consisting of:

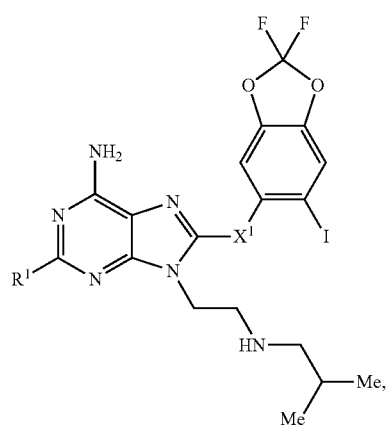

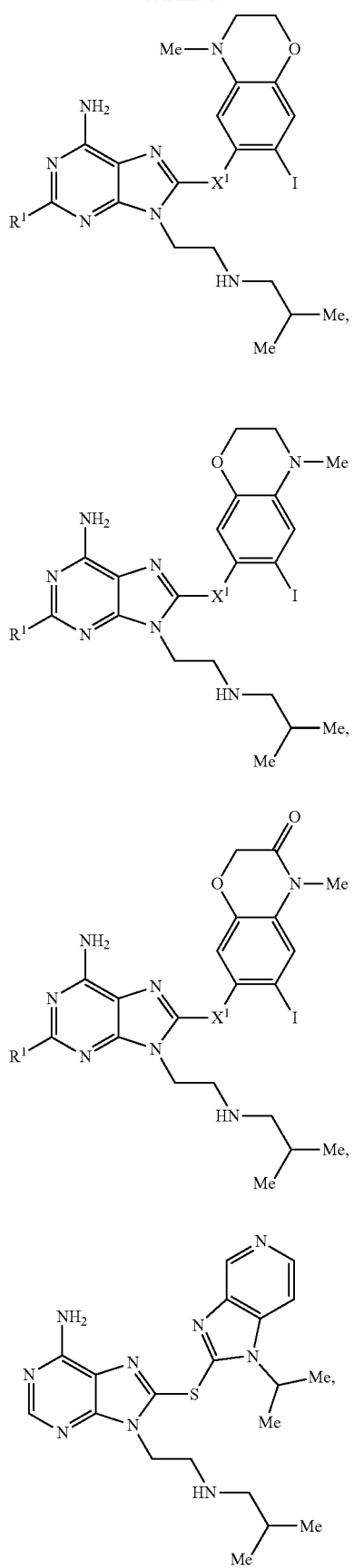
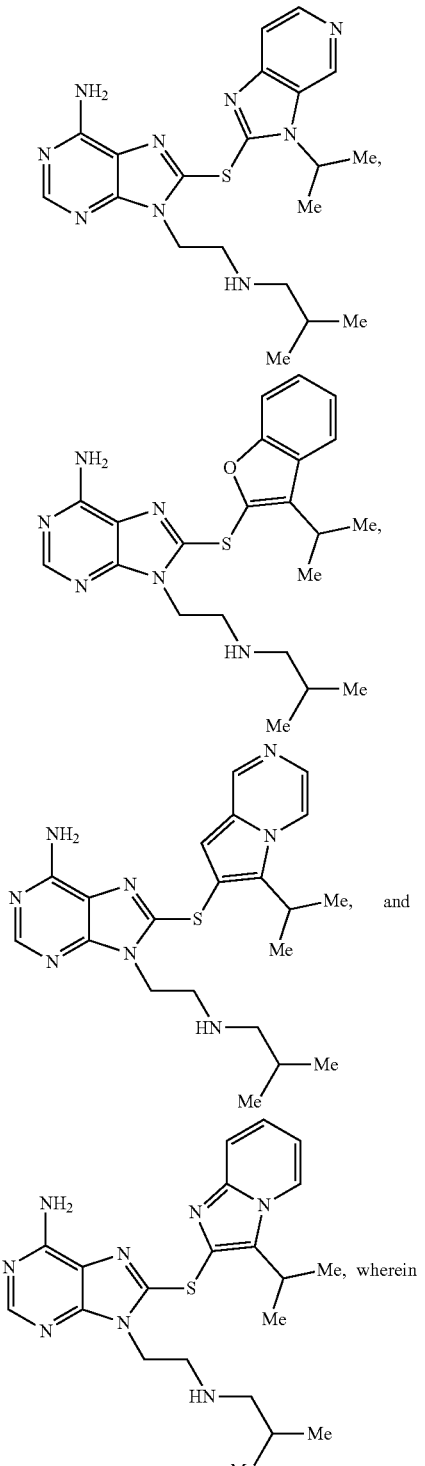
when $X^1$ is S, $R^1$ is H, and
when $X^1$ is $CH_2$, $R^1$ is F.
In other embodiments, the compound is selected from the group consisting of:

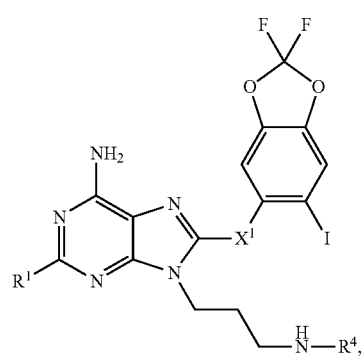
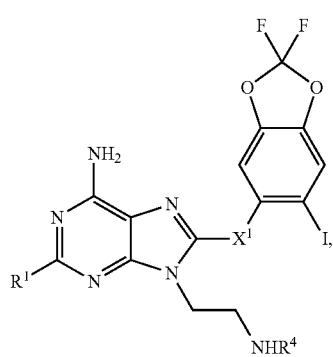
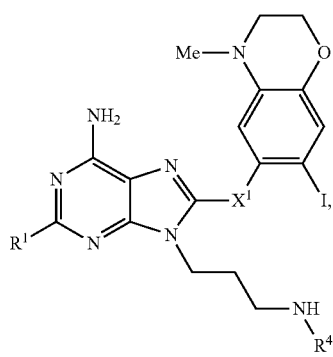
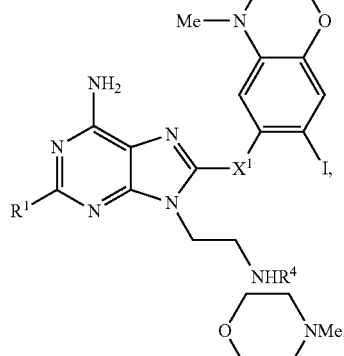
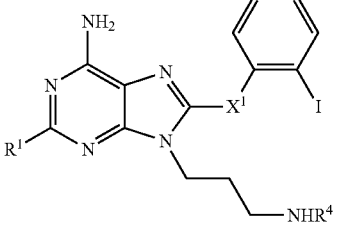
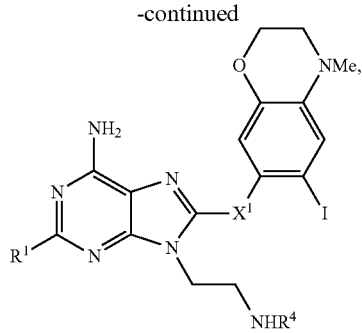
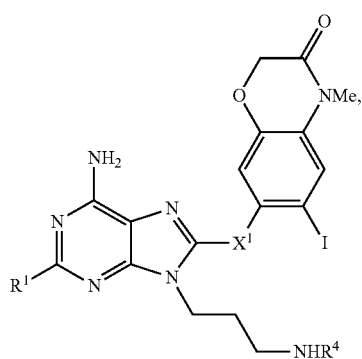
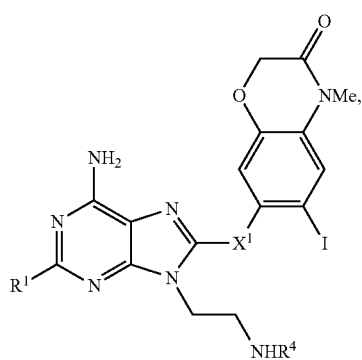
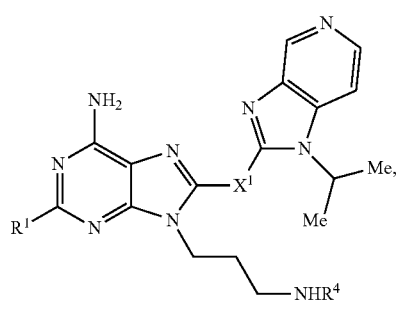
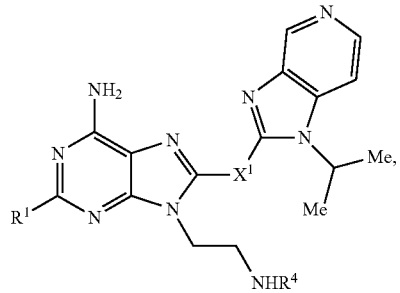

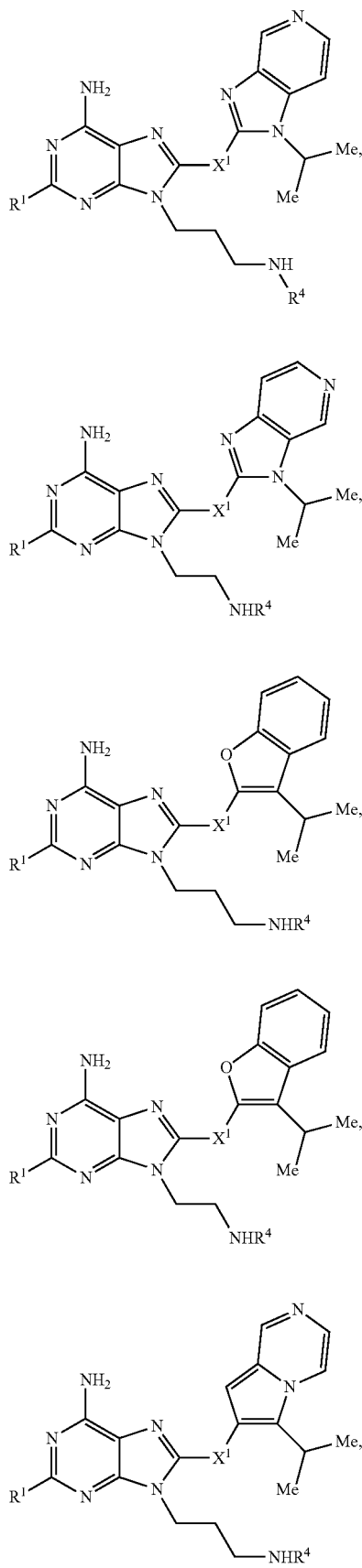

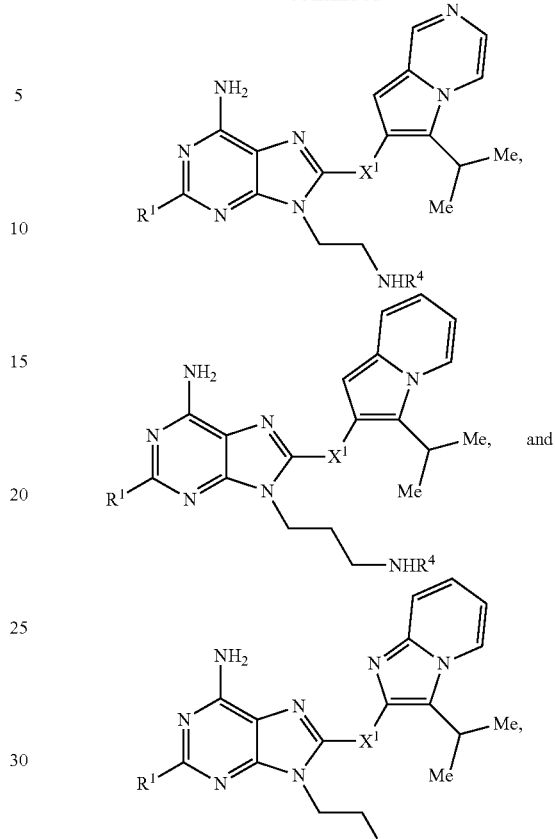

wherein
$R^4$ is $C_{1-6}$ alkyl, and when $X^1$ is S, $R^1$ is H, and when $X^1$ is $CH_2$, $R^1$ is F. In some embodiments, $R^4$ is methyl, ethyl, n-propyl, isopropyl, n-butyl, isobutyl, tert-butyl, sec-butyl, n-pentyl, isopentyl, neopentyl, or n-hexyl. In some embodiments, these $R^4$ groups are substituted with 1, 2, or 3 substituent groups as defined herein.

The invention also features a pharmaceutical composition that includes one or more of the compounds described above (or a tautomer or pharmaceutically acceptable salt, solvate, or prodrug thereof), and one or more pharmaceutically acceptable excipients.

The invention also features a kit that includes one or more of the above-described compounds and pharmaceutical compositions, and instructions for use to treat a condition in a subject.

The invention also features a method of treating a condition in a subject by administering one or more of the above-described compounds and pharmaceutical compositions to the subject in a dosage sufficient to inhibit Hsp90.

Conditions that can be treated with the compounds of the invention include neurodegenerative disorders and cell proliferative disorders, such as Alzheimer's disease, Parkinson's disease, Huntington's disease, or cancer.

The term "$C_{1-6}$alkoxy" represents a chemical substituent of formula —OR, where R is a $C_{1-6}$ alkyl group, unless otherwise specified. In some embodiments, the alkyl group can be further substituted with 1, 2, 3, or 4 substituent groups as defined herein.

The term "$C_{1-6}$alkoxy $C_{1-6}$alkyl" represents an alkyl group that is substituted with an alkoxy group. Exemplary unsubstituted alkoxyalkyl groups include between 2 to 12 carbons.

In some embodiments, the alkyl and the alkoxy each can be further substituted with 1, 2, 3, or 4 substituent groups as defined herein for the respective group.

The term "$C_{1-6}$alkyl," as used herein, is inclusive of both straight chain and branched chain saturated groups of from 1 to 6 carbons, unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents as described herein.

The term "alkylene" and the prefix "alk-," as used herein, represent a saturated divalent $C_{1-10}$ hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, or 10. In some embodiments, the alkylene can be further substituted with 1, 2, 3, or 4 substituent groups as defined herein for an alkyl group.

The term "alk$C_{3-9}$cycloalkyl" represents a $C_{3-9}$cycloalkyl group, as defined herein, attached to the parent molecular group through an alkylene group, as defined herein (e.g., an alkylene group of 1-4, 1-6, or 1-10 carbons). In some embodiments, the alkylene and the cycloalkyl each can be further substituted with 1, 2, 3, or 4 substituent groups as defined herein for the respective group.

The term "$C_{1-6}$alkylsulfonyl," as used herein, represents an alkyl group attached to the parent molecular group through an —S(O)$_2$— group. Exemplary unsubstituted alkylsulfinyl groups are of from 1 to 6 carbons. In some embodiments, the alkyl group can be further substituted with 1, 2, 3, or 4 substituent groups as defined herein.

The term "$C_{1-6}$alkylthio," as used herein, represents a chemical substituent of formula —SR, where R is an alkyl group. In some embodiments, the alkyl group can be further substituted with 1, 2, 3, or 4 substituent groups as described herein for alkyl groups.

The term "amino," as used herein, represents —N(R$^{N1}$)$_2$, wherein each R$^{N1}$ is, independently, H or alkyl, or two R$^{N1}$ combine to form a heterocyclyl. The term "$C_{1-6}$alkylamino" refers to an amino group where one R$^{N1}$ is H and the other R$^{N1}$ is alkyl. The term "di($C_{1-6}$alkyl)amino" refers to an amino group where each R$^{N1}$ is alkyl.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents The term "$C_{3-9}$cycloalkyl," as used herein represents a monovalent saturated or unsaturated non-aromatic cyclic hydrocarbon group of from three to nine carbons, unless otherwise specified, and is exemplified by cyclopropyl, cyclobutyl, cyclopentyl, cyclohexyl, cycloheptyl, bicyclo[2.2.1.]heptyl, and the like. Cycloalkyl groups may be optionally substituted with, for example, one, two, three, or four substituents as described herein.

The term an "effective amount" of an agent, as used herein, is that amount sufficient to effect beneficial or desired results, such as clinical results, and, as such, an "effective amount" depends upon the context in which it is being applied. For example, in the context of administering an agent that is an inhibitor of Hsp90, an effective amount of an agent is, for example, an amount sufficient to achieve a reduction in Hsp90 activity as compared to the response obtained without administration of the agent.

The term "$C_{1-6}$fluoroalkoxy," as used herein, represents an alkoxy group, as defined herein, where one or more hydrogen radicals (e.g., 1, 2, 3, or all hydrogen radicals) bound to the alkoxy group has been replaced by a fluoride radical.

The term "$C_{1-6}$haloalkoxy," as used herein, represents an alkoxy group, as defined herein, substituted by a halogen group (i.e., F, Cl, Br, or I). A haloalkyl may be substituted with one, two, three, or, in the case of alkyl groups of two carbons or more, four halogens. $C_{1-6}$haloalkoxy groups include fluoroalkoxy groups. In some embodiments, the $C_{1-6}$haloalkoxy group can be further substituted with 1, 2, 3, or 4 substituent groups as described herein for alkoxy groups.

The term "$C_{1-6}$haloalkyl," as used herein, represents an alkyl group, as defined herein, substituted by a halogen group (i.e., F, Cl, Br, or I). A $C_{1-6}$haloalkyl may be substituted with one, two, three, or, in the case of alkyl groups of two carbons or more, four halogens. $C_{1-6}$haloalkyl groups include perfluoroalkyls. In some embodiments, the $C_{1-6}$haloalkyl group can be further substituted with 1, 2, 3, or 4 substituent groups as described herein for alkyl groups.

The term "halogen," as used herein, represents a group selected from fluorine (—F), chlorine (—Cl), bromine (—Br), and iodine (—I).

The term "3-9 membered heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" also includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like.

The term "heteroaryl," as used herein, represents that subset of heterocyclyls, as defined herein, which are aromatic:

i.e., they contain 4n+2 pi electrons within the mono- or multicyclic ring system. In some embodiments, the heteroaryl is substituted with, e.g., 1, 2, 3, or 4 substituent groups as defined herein.

The term "hydroxy," as used herein, represents an —OH group.

The term "hydroxyC$_{1-6}$alkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl, and the like.

The term "pharmaceutical composition," as used herein, represents a composition containing a compound described herein, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

The term "prevent," as used herein, refers to prophylactic treatment or treatment that prevents one or more symptoms or conditions of a disease, disorder, or conditions described herein. Preventive treatment that includes administration of a compound described herein, or a pharmaceutically acceptable salt or solvate thereof, or a pharmaceutical composition thereof, can be acute, short-term, or chronic. The doses administered may be varied during the course of preventative treatment.

The term "prodrug," as used herein, represents compounds that are rapidly transformed in vivo to the parent compound of the above formula, for example, by hydrolysis in blood. Prodrugs of the compounds described herein may be conventional esters. Some common esters that have been utilized as prodrugs are phenyl esters, aliphatic ($C_1$-$C_8$ or $C_8$-$C_{24}$) esters, cholesterol esters, acyloxymethyl esters, carbamates, and amino acid esters. For example, a compound that contains an OH group may be acylated at this position in its prodrug form.

A thorough discussion is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference. Preferably, prodrugs of the compounds of the present invention are suitable for use in contact with the tissues of humans and animals with undue toxicity, irritation, allergic response, and the like, commensurate with a reasonable benefit/risk ratio, and effective for their intended use.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Asymmetric or chiral centers may exist in any of the compounds of the present invention. The present invention contemplates the various stereoisomers and mixtures thereof. Individual stereoisomers of compounds of the present invention are prepared synthetically from commercially available starting materials that contain asymmetric or chiral centers or by preparation of mixtures of enantiomeric compounds followed by resolution well known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns or by chiral HPLC methods. Methods of chiral separations have been described previously (G. B. Cox (ed.) in *Preparative Enantioselective Chromatography*, 2005, Blackwell Publishing). Alternatively, chiral compounds can be prepared by an asymmetric synthesis that favors the preparation of one enantiomer over the other. Alternatively a chiral pool synthesis (starting with an enantiomerically pure building block) can be used wherein the chiral group or center is retained in the intermediate or final product. Enantiomers are designated herein by the symbols "R," or "S," depending on the configuration of substituents around the chiral atom. Alternatively, enantiomers are designated as (+) or (−) depending on whether a solution of the enantiomer rotates the plane of polarized light clockwise or counterclockwise, respectively.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, where the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified.

Other features and advantages will be apparent from the following description and the claims.

Procedures for making compounds described herein are provided below with reference to Schemes 1-4. In the reactions described below, it may be necessary to protect reactive functional groups (such as hydroxy, amino, thio or carboxy groups) to avoid their unwanted participation in the reactions. The incorporation of such groups, and the methods required to introduce and remove them are known to those skilled in the art (for example, see Greene, Wuts, *Protective Groups in Organic Synthesis,* 2nd Ed. (1999)). The deprotection step may be the final step in the synthesis such that the removal of protecting groups affords compounds of formula (1) as disclosed herein. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of formula (1) in which X represents S may be prepared as described by Zhang et al. (*J. Med. Chem.* 2006, 49, 5352-5362), Llauger et al. (*J. Med. Chem.* 2005, 48, 2892-2905), Biamonte et al. (*J. Med. Chem.* 2006, 49, 817-828), and illustrated in Scheme 1.

Scheme 1.

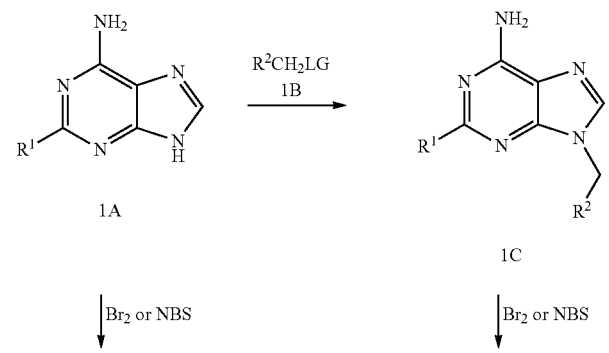

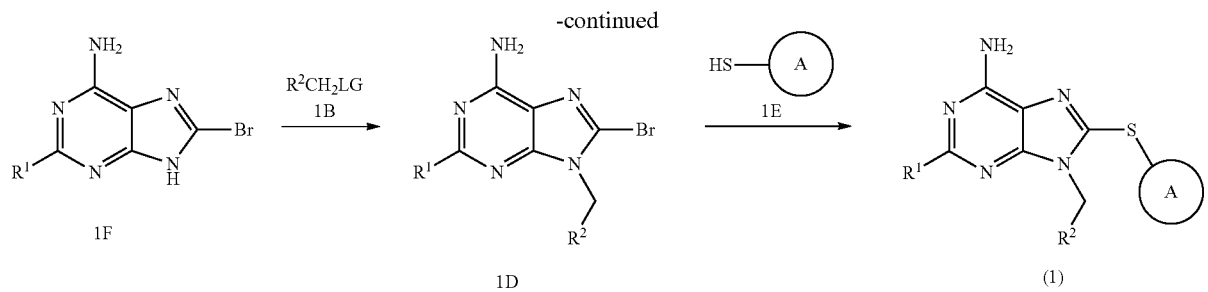

Purines of formula 1A are either commercially available or can be prepared using standard routes known to those skilled in the art. Alkylation of purines of formula 1A by alkylating reagents of formula 1B to provide compounds of formula 1C can be carried out using any conditions known to those skilled in the art, for example by using a suitable base, such as cesium carbonate, in an appropriate solvent, such as dimethylformamide at a suitable temperature, such as room temperature. LG in formula 1B represents any suitable leaving group, such as a halogen or a suitable sulphonyl ester, such as mesylate or tosylate. Alkylating agents represented by formula 1B are either commercially available or may be prepared using standard methods known to those skilled in the art. Alternatively, the alkylation may be carried out under Mitsunobu conditions using a reagent of formula 1B in which LG is a hydroxyl group in the presence of a suitable phosphine, such as triphenyl phosphine and an appropriate dehydrating agent such as diethylazodicarboxylate in a suitable solvent such as toluene at a suitable temperature such as room temperature. Compounds of formula 1C can be brominated under standard conditions known to those skilled in the art to provide compounds of formula 1D. Suitable conditions include the use of a brominating agent such as bromine or N-bromosuccinamide in an appropriate solvent such as dimethylformamide at an appropriate temperature such as room temperature. Compounds of formula 1D can be reacted with compounds of formula 1E to provide compounds of formula (1) using any suitable conditions known to those skilled in the art, for example by heating the compounds together in a suitable solvent, such as dimethylformamide at a suitable temperature, such as 100° C. Optionally this reaction may be carried out in the presence of an appropriate base, such as potassium t-butoxide. Alternatively compounds of formula 1C and 1D may be heated together in the absence of solvent at a suitable temperature, such as 150° C. Alternatively, purines of formula 1A can be brominated to provide compounds of formula 1F, which can then be alkylated to provide compounds of formula 1D. Compounds of formula 1E can be prepared using any suitable method known to those skilled in the art, for example by using the method illustrated in Scheme 2.

Scheme 2.

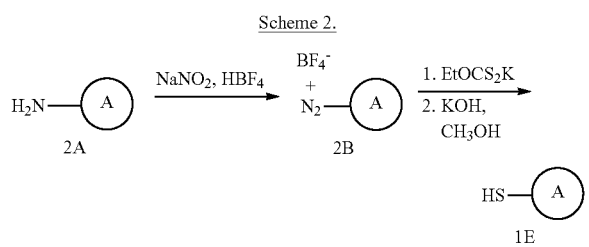

Amines of formula 2A can be converted into diazonium salts of formula 2B using any method known to those skilled in the art, for example by using sodium nitrite, hydrochloric acid and hydrogen tetrafluoroborate in a suitable solvent such as water at an appropriate temperature such as 0° C., as described by Biamonte et al (*J. Org. Chem.* 70:717-720, 2005). Diazonium salts of formula 2B can be converted into thiols of formula 1E using a variety of methods known to those skilled in the art. These include treatment of the diazonium salt of formula 2B with a range of sulphur nucleophiles (such as $S_n^{2-}$, $NCS^-$, $S_2O_3^-$, $EtOCS_2^-$ or thiourea) followed by hydrolysis with alkali (such as potassium hydroxide) as described by Biamonte et al. (*J. Org. Chem.* 70:717-720, 2005, and *J. Med. Chem.* 49:817-828, 2006). The amines of formula 2A are either commercially available or may be prepared using an appropriate method known to those skilled in the art or reported in the literature.

An alternative approach to the synthesis of compounds of formula (1) in which X represents S is illustrated in Scheme 3 and has been reported by Llauger et al. (*J. Med. Chem.* 48:2892-2905, 2005), He et al. (*J. Med. Chem.* 49:381-390, 2006) and Biamonte et al. (*J. Med. Chem.* 49:817-828, 2006, and *J. Org. Chem.* 70:717-720, 2005).

Scheme 3.

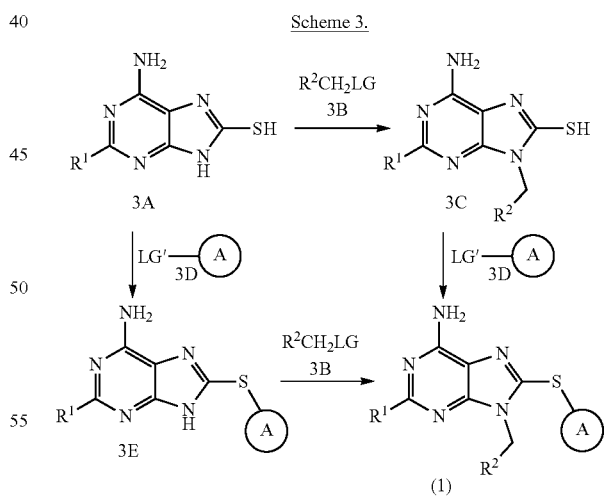

Purines of formula 3A are either commercially available or can be prepared using standard routes known to those skilled in the art. Alkylation of purines of formula 3A by alkylating reagents of formula 3B to provide compounds of formula 3C can be carried out using any conditions known to those skilled in the art, for example by using a suitable base, such as cesium carbonate, in an appropriate solvent, such as dimethylformamide at a suitable temperature, such as room temperature. LG in formula 3B represents any suitable leaving group, such as a halogen or a suitable sulphonyl ester, such as mesylate or tosylate. Alkylating agents represented by formula 3B are either commercially available or may be prepared using standard methods known to those skilled in the art. Alternatively, the alkylation may be carried out under Mitsunobu conditions using a reagent of formula 3B in which LG is a hydroxyl Compounds of formula (1) in which X represents $CH_2$ may be prepared as reported by He et al. (*J. Med. Chem.* 49:381-390, 2006), Biamonte et al. (*J. Med. Chem.* 49:817-828, 2006), Dymock et al. (*Bioorg. Med. Chem. Lett.* 14:325-328, 2004), Tao et al. (*Bioorg. Med. Chem. Lett.* 19:415-417, 2009) and Chiosis et al. (*Bioorg. Med. Chem.* 10:3555-3564, 2002), and illustrated in Scheme 4.

Scheme 4.

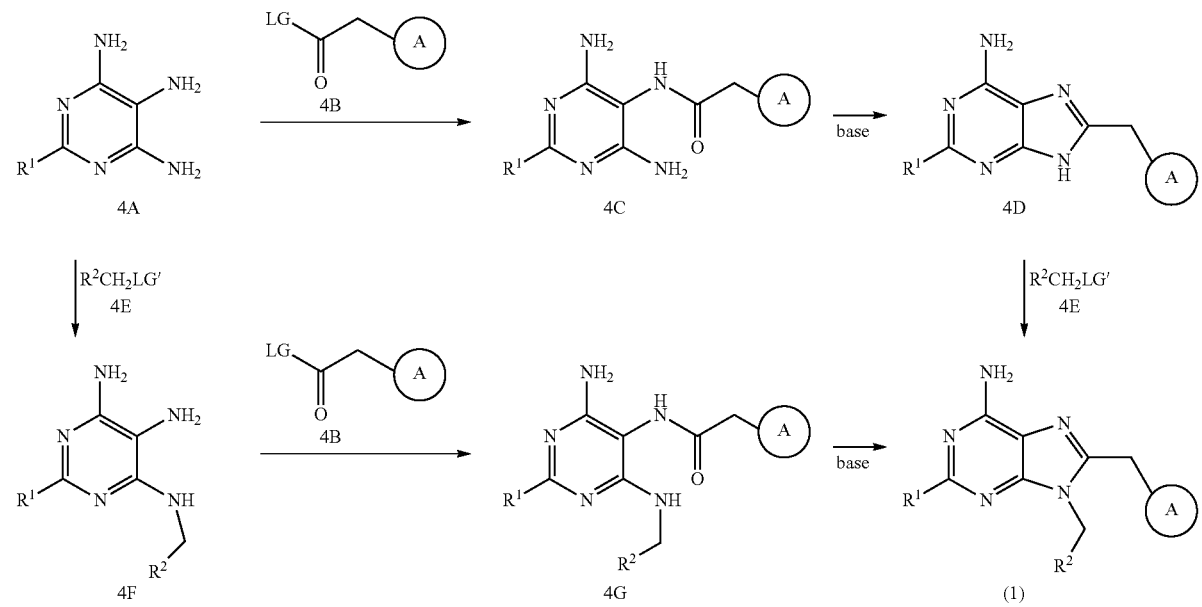

group in the presence of a suitable phosphine, such as triphenyl phosphine and an appropriate dehydrating agent such as diethylazodicarboxylate in a suitable solvent such as toluene at a suitable temperature such as room temperature. Compounds of formula 3C may be converted into compounds of formula (1) by using a reagent of formula 3D under any suitable conditions known to those skilled in the art. Reagents of formula 3D include diazonium salts (in which LG' represents $N_2$), as shown in Scheme 2, and iodides (in which LG' represents I). Reaction of a compound of formula 3C with a diazonium salt of formula 3D may be carried out in a suitable solvent, such as dimethylsulphoxide at a suitable temperature, such as room temperature, optionally in the presence of a base such as di-isopropylethylamine, as described by Biamonte et al. (*J. Org. Chem.* 70:717-720, 2005). Reaction of a compound of formula 3C with an iodide of formula 3D may be carried out under copper catalysed coupling conditions using neocuproine and copper iodide in the presence of a suitable base such as sodium t-butoxide in a suitable solvent, such as dimethylformamide or ethylene glycol at elevated temperature, such as 110° C.-130° C., as described by He et al. (*J. Org. Chem.* 69:3230-3232, 2004 and *J. Med. Chem.* 49:381-390, 2006) or Llauger et al. (*J. Med. Chem.* 48:2892-2905, 2005) and Gwong et al. (*Org. Lett.* 4:3517-3520, 2002). Alternatively, purines of formula 3A may be reacted with a reagent of formula 3D to provide compounds of formula 3E, which can then be alkylated to provide compounds of formula (1). Diazonium salts of formula 3D may be prepared from the corresponding amine as shown in Scheme 2. Iodides of formula 3D may be commercially available or may be prepared using standard procedures reported in the literature, or known to those skilled in the art.

Diaminopyrimidines of formula 4A can be reacted with acylating agents of formula 4B to provide amides of formula 4C using any standard method known to those skilled in the art. For example, if LG in formula 4B is OH, the reaction may be carried out by using standard coupling conditions. Appropriate conditions involve the use of a suitable base, such as di-isopropylethylamine in the presence of an appropriate coupling agent, such as O-benzotriazol-1-yl-N,N,N',N'-tetramethyluronium hexafluorophosphate in a suitable solvent such as dimethylformamide at a suitable temperature such as room temperature as described by Dymock et al. (*Bioorg. Med. Chem.* 14:325-328, 2004). Alternatively, if LG in formula 4B is F, the reaction may be conducted in the presence of a suitable base, such as potassium carbonate and dimethylaminopyridine or di-isopropylethylamine in a suitable solvent such as dimethylformamide at an appropriate temperature, such as 120° C., as described by He et al. (*J. Med. Chem.* 49:381-390, 2006) and Chiosis et al. (*Bioorg. Med. Chem. Lett.* 10:3555-3564, 2002). In an another alternative, if LG in formula 4B is Cl, the reaction may be carried in N-methylpyrrolidine at elevated temperature, such as 40-50° C., as described by Biamonte et al. (*J. Med. Chem.* 49:817-828, 2006). Diaminopyrimidines of formula 4A and reagents of formula 4B may be commercially available or may be prepared using any standard method known to those skilled in the art or reported in the literature.

Amides of formula 4C may be cyclised to form purines of formula 4D using any suitable method known to those skilled in the art. Suitable methods involve the use of an appropriate base, such as sodium methoxide or ammonia, in an appropriate solvent such as n-butanol, methanol (or a mixture of the two), i-butanol or ethanol at a suitable temperature such as 100-120° C. or the reflux temperature of the solvent. Purines of formula 4D may be alkylated to provide compounds of formula (1) by using alkylating reagents of formula 4E using any conditions known to those skilled in the art, for example by using a suitable base, such as cesium carbonate, in an appropriate solvent, such as dimethylformamide at a suitable temperature, such as room temperature. LG' in formula 4E represents any suitable leaving group, such as a halogen or a suitable sulphonyl ester, such as mesylate or tosylate. Alkylating agents represented by formula 4E are either commercially available or may be prepared using standard methods known to those skilled in the art. Alternatively, the alkylation may be carried out under Mitsunobu conditions using a reagent of formula 4E in which LG' is a hydroxyl group, in the presence of a suitable phosphine, such as triphenyl phosphine and an appropriate dehydrating agent such as diethylazodicarboxylate in a suitable solvent such as toluene at a suitable temperature such as room temperature.

Alternatively, diaminopyrimidies of formula 4A may be alkylated using alkylating agents of formula 4E to provide compounds of formula 4F. Compounds of formula 4F can be converted into compounds of formula (1) by reaction with a reagent of formula 4B to form compounds of formula 4G followed by cyclisation.

Compounds of any of formulas (1) or any of the intermediates described in the schemes above, can be further derivatized by using one or more standard synthetic methods known to those skilled in the art. Such methods can involve substitution, oxidation or reduction reactions. These methods can also be used to obtain or modify compounds of formula (1) or any preceding intermediates by modifying, introducing or removing appropriate functional groups. Particular substitution approaches include alkylation, arylation, heteroarylation, acylation, thioacylation, halogenation, sulphonylation, nitration, formylation, hydrolysis and coupling procedures. These procedures can be used to introduce a functional group onto the parent molecule (such as the nitration or sulphonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent such as tetrahydrofuran in the presence of a phosphine (such as triphenylphosphine) and a dehydrating agent (such as diethyl-, diisopropyl- or dimethylazodicarboxylate). Alternatively, ether groups can be prepared by deprotonation of an alcohol, using a suitable base (such as sodium hydride) followed by the addition of an alkylating agent (such as an alkyl halide or an alkylsulphonate).

In another example, a primary or secondary amine can be alkylated using a reductive alkylation process. For example, the amine can be treated with an aldehyde and a borohydride (such as sodium triacetoxyborohydride, or sodium cyanoborohydride) in a solvent (such as a halogenated hydrocarbon, for example dichloromethane, or an alcohol, for example ethanol) and, where necessary, in the presence of an acid (such as acetic acid).

In another example, —OH groups may be generated from the corresponding ester, acid, acid chloride or aldehyde by reduction with a suitable reducing agent, such as a complex metal hydride such as lithium aluminium hydride in a solvent such as tetrahydrofuran.

In another example, hydroxy groups (including phenolic OH groups) can be converted into leaving groups such as halogen atoms or sulphonyloxy groups (such as alkylsulphonyloxy, for example trifluoromethylsulphonyloxy, or arylsulphonyl, for example p-toluenesulphonyloxy) using conditions known to those skilled in the art. For example, an aliphatic alcohol can be reacted with thionyl chloride in a halogenated hydrocarbon (such as dichloromethane) to afford the corresponding alkylchloride. A base (such as triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxan). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyl lithium) optionally at a low temperature (such as −78° C.) in a solvent (such as tetrahydrofuran) and the mixture may then quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, aromatic halogen substituents in the compounds may participate in a range of metal catalysed reactions to introduce alternative functional groups such as amines, amides, ethers, thiols, aryl groups or heteroaryl groups.

Particular oxidation approaches include dehydrogenations and aromatisation, and the addition of oxygen to certain functional groups. For example, aldehyde groups can be prepared by oxidation of the corresponding alcohol using conditions well known to those skilled in the art. For example, an alcohol can be treated with an oxidising agent (such as the Dess-Martin reagent) in a solvent (such as a halogenated hydrocarbon, for example dichloromethane). Alternative oxidising conditions can be used, such as treatment with oxalyl chloride and an activating amount of dimethylsulphoxide and subsequent quenching by the addition of an amine (such as triethylamine). Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulphur atoms can be oxidised to the corresponding sulphoxide or sulphone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups, saturation (or partial saturation) of unsaturated compounds including aromatic rings. For example, primary alcohols can be generated from the corresponding ester or aldehyde by reduction, using a metal hydride (such as lithium aluminium hydride or sodium borohydride in a solvent such as methanol). Alternatively, —OH groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as tin or iron) in the presence of an acid (such as hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Pharmaceutical Compositions

The compounds used in the methods described herein are preferably formulated into pharmaceutical compositions for administration to human subjects in a biologically compatible form suitable for administration in vivo. Pharmaceutical compositions typically include a compound as described herein and a pharmaceutically acceptable excipient.

The compounds described herein can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds used in the methods described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

Dosages

The dosage of the compound used in the methods described herein, or pharmaceutically acceptable salts or prodrugs thereof, or pharmaceutical compositions thereof, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds used in the methods described herein may be administered initially in a suitable dosage that may be adjusted as required, depending on the clinical response. In general, a suitable daily dose of a compound of the invention will be that amount of the compound that is the lowest dose effective to produce a therapeutic effect. Such an effective dose will generally depend upon the factors described above.

A compound of the invention may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule. An active compound may be administered, for example, 1, 2, 3, 4, 5, 6, 7, 8, 9, 10, 11, or 12 times per day, every $2^{nd}$, $3^{rd}$, $4^{th}$, $5^{th}$, or $6^{th}$ day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions.

While the attending physician ultimately will decide the appropriate amount and dosage regimen, an effective amount of a compound of the invention may be, for example, a total daily dosage of, e.g., between 0.05 mg and 3000 mg of any of the compounds described herein. Alternatively, the dosage amount can be calculated using the body weight of the patient. Such dose ranges may include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

In the methods of the invention, the time period during which multiple doses of a compound of the invention are administered to a patient can vary. For example, in some embodiments doses of the compounds of the invention are administered to a patient over a time period that is 1-7 days; 1-12 weeks; or 1-3 months. In other embodiments, the compounds are administered to the patient over a time period that is, for example, 4-11 months or 1-30 years. In other embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

Pharmaceutical Compositions

For human use, a compound of the invention can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of Formula (1) into preparations which can be used pharmaceutically.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, $21^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, 6th Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Pharmaceutical Formulations

A compound identified as capable of treating any of the conditions described herein, using any of the methods described herein, may be administered to patients or animals with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a disease in which necrosis occurs. Administration may begin before the patient is symptomatic.

Exemplary routes of administration of the compounds (e.g., the compounds having Formula (1)), or pharmaceutical compositions thereof, used in the present invention include oral, sublingual, buccal, transdermal, intranasal, inhalation, topical, and parenteral (e.g., intravenous) administration. The compounds desirably are administered with a pharmaceutically acceptable carrier. Pharmaceutical formulations of the compounds described herein formulated for treatment of the disorders described herein are also part of the present invention.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for Buccal Administration

Dosages for buccal or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of compounds of the invention. Desirably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598 and Biesalski, U.S. Pat. No. 5,556,611, each of which is herein incorporated by reference).

Formulations for Nasal or Inhalation Administration

The compounds may also be formulated for nasal administration. Compositions for nasal administration also may conveniently be formulated as aerosols, drops, gels, and powders. The formulations may be provided in a single or multi-dose form. In the case of a dropper or pipette, dosing may be achieved by the patient administering an appropriate, predetermined volume of the solution or suspension. In the case of a spray, this may be achieved, for example, by means of a metering atomizing spray pump.

The compounds may further be formulated for aerosol administration, particularly to the respiratory tract by inhalation and including intranasal administration. The compound will generally have a small particle size for example on the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example, a powder mix of the compound in a suitable powder base such as lactose, starch, and starch derivatives such as hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Formulations for Parenteral Administration

The compounds described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., a compound of Formula (1), (I-a), (I-a-1), or (I-a-2), or any of Compounds (1a)-(1n)), or a solution thereof (2) "Drug for Injection:" the drug substance (e.g., a compound of Formula (1), (I-a), (I-a-1), or (I-a-2), or any of Compounds (1a)-(1n)) as a dry solid that will be combined with the appropriate sterile vehicle for parenteral administration as a drug injection;

(3) "Drug Injectable Emulsion:" a liquid preparation of the drug substance (e.g., a compound of Formula (1), (I-a), (I-a-1), or (I-a-2), or any of Compounds (1a)-(1n)) that is dissolved or dispersed in a suitable emulsion medium;

(4) "Drug Injectable Suspension:" a liquid preparation of the drug substance (e.g., a compound of Formula (1), (I-a), (I-a-1), or (I-a-2), or any of Compounds (1a)-(1n)) suspended in a suitable liquid medium; and (5) "Drug for Injectable Suspension:" the drug substance (e.g., a compound of Formula (1), (I-a), (I-a-1), or (I-a-2), or any of Compounds (1a)-(1n)) as a dry solid that will be combined with the appropriate sterile vehicle for parenteral administration as a drug injectable suspension.

Exemplary formulations for parenteral administration include solutions of the compound prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels. suspension, or as an oil-based solution.

Methods of Treatment

The compounds and compositions described herein can be used in the treatment of conditions and disorders in which Hsp90 has been implicated, e.g., cell proliferative disorders such as cancers, neurodegenerative diseases such as taupathies, and viral infections.

Cell Proliferative Disorders

Hsp90 has emerged as a key therapeutic target for cancer therapy due to the involvement of this multichaperone complex in various pathogenic cellular processes (e.g., Solit et al., *Drug Discovery Today*, 13:38-43 (2008) and Taldone et al., *Current Opinion in Pharmacology*, 8:370-374 (2008)). Hsp90 client proteins include those implicated in: acute myeloid leukemia (Flt-3), breast cancer (HER2), chronic lymphoid leukemia (Zap70), chronic myeloid leukemia (Bcr-Abl or mBcr-Abl), gastrointestinal stromal tumor (c-Kit), gastric cancer (c-Met), glioblastoma (mutant EGFR or c-Met), lung cancer (c-Met), lymphoma (NMP-ALK), melanoma (Raf-1/mutant BRAF), myeloma (IGF-1R/Akt), non-small cell lung cancer (mutant EGFR), renal cancer, (HIF-1α), and small cell lung cancer (Akt). See, for example, Solit et al., *Drug Discovery Today*, 13:38-43 (2008) and Whitesell et al., *Nature Reviews Cancer*, 5:761-772 (2005). Still other cell proliferative disorders that may be treated by the inhibition of Hsp90 include: blast-phase chronic myelogenous leukemia, leukemia, lymphoproliferative disorder, metastatic melanoma, multiple myeloma (e.g., relapsed or refractory multiple myeloma), myeloproliferative disorders, pancreatic cancer, small intestine cancer, and solid tumor. Moreover, cancer cells have been shown to be more sensitive to Hsp90 inhibition than non-pathogenic cells.

Accordingly, the compounds described herein can be useful treatments for cell proliferative disorders.

Neurodegenerative Diseases

Increased levels of Hsp90 have been implicated in neurodegenerative disorders. For example, aberrant Hsp90 activity has been shown in tauopathies, which are conditions characterized by accumulation of abnormal Tau proteins (e.g., hyperphosphorylated and aggregated Tau; see Delacourte et al., *Current Opinion in Neurology*, 13:371-376 (2000), and Sergeant et al, *Biochimica et Biophysica Acta*, 1739:179-197 (2005)). See, e.g., Luo et al., *Proceedings of the National Academy of Science*, 104:9511-9516 (2007). Many mouse models of tauopathies are known in the art (see, e.g., Ballatore et al., *Nature Reviews Neuroscience*, 8:663-672 (2007).

Accordingly, compounds and compositions described herein can be useful for the treatment of neurodegenerative diseases and tauopathies that include argyrophilic grain disease, Alzheimer's disease (AD), amyotrophic lateral sclerosis, corticobasal degeneration, dementia pugislistica, Down's syndrome, familial British dementia, frontal lobe degeneration (dementia lacking distinctive histopathological features), frontotemporal dementia (FTD; e.g., fronto-temporal dementia with parkinsonism linked to chromosome 17 (FTDP-17)), hippocampal tauopathy in cerebral aging, myotonic dystrophy of type I, Niemann—Pick disease of type C, Parkinson's disease (e.g., parkinsonism-dementia complex of Guam, Parkinsonism with dementia of Guadeloupe, or postencephalitic parkinsonism), Pick's disease (PiD), and progressive supranuclear palsy.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound having a structure according to the following formula,

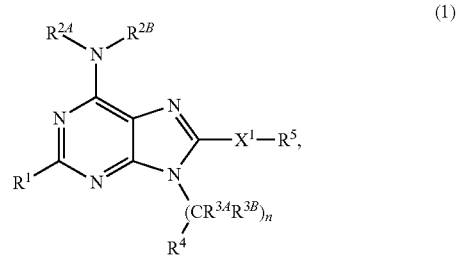

(1)

or a tautomer or pharmaceutically acceptable salt, or solvate thereof, wherein $R^1$ is H, halogen, CN, $C_{1-6}$alkoxy, $C_{1-6}$fluoroalkoxy, or $C_{1-6}$alkyl;

$R^{2A}$ and $R^{2B}$ are each H;

each $R^{3A}$ and $R^{3B}$ is, independently, H, halogen, or $C_{1-6}$alkyl;

n is 1, 2, 3, or 4;

$R^4$ is H, $C_{3-9}$cycloalkyl or $NR^{4A}R^{4B}$;

$R^{4A}$ and $R^{4B}$ are each, independently, H or $C_{1-6}$alkyl;

$X^1$ is $CH_2$, S, or SO;

$R^5$ is a bicyclic heteroaryl selected from Substructures A, B, and D wherein (a) Substructure A is selected from

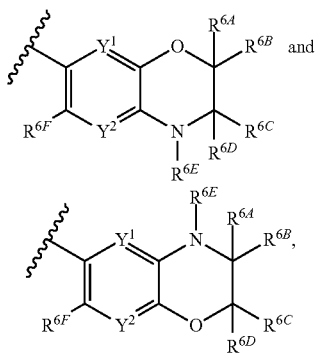

wherein
each of $R^{6A}$, $R^{6B}$, $R^{6C}$, and $R^{6D}$ is, independently, H or $C_{1-6}$alkyl, or $R^{6A}$ and $R^{6B}$, or $R^{6C}$ and $R^{6D}$, combine to form =O or $C_{3-9}$cycloalkyl, $R^{6E}$ is H, $C_{1-6}$alkyl, or alk$C_{3-9}$cycloalkyl, $R^{6F}$ is H, halogen, $C_{1-6}$alkyl, $C_{1-6}$haloalkyl, $C_{1-6}$alkoxy, $C_{1-6}$haloalkoxy, $C_{1-6}$alkylthio, $C_{1-6}$alkylsulfonyl, $C_{1-6}$alkylamino, or di($C_{1-6}$alkyl)amino;

$Y^1$ and $Y^2$ are, independently, N or $CR^{6G}$, and $R^{6G}$ is H, halogen, CN, $C_{1-6}$alkyl, $C_{1-6}$haloalkyl, $C_{1-6}$alkoxy, $C_{1-6}$haloalkoxy, hydroxy$C_{1-6}$ alkyl, or $C_{1-6}$alkoxy-$C_{1-6}$ alkyl;

(b) Substructure B is selected from

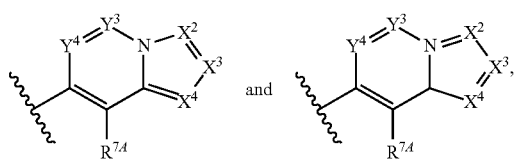

wherein
$R^{7A}$ is H, halogen, $C_{1-6}$alkyl, $C_{1-6}$haloalkyl, $C_{1-6}$alkoxy, $C_{1-6}$haloalkoxy, $C_{1-6}$alkylthio, $C_{1-6}$alkylsulfonyl, $C_{1-6}$alkylamino, or di($C_{1-6}$alkyl)amino, $Y^3$ and $Y^4$ are, independently, N or $CR^{7B}$, each $X^2$, $X^3$, and $X^4$ is, independently, N or $CR^{7C}$, each $R^{7B}$ and $R^{7C}$ is, independently, H, halogen, CN, $C_{1-6}$alkyl, $C_{1-6}$haloalkyl, $C_{1-6}$alkoxy, $C_{1-6}$haloalkoxy, hydroxy$C_{1-6}$ alkyl, or $C_{1-6}$alkoxy-$C_{1-6}$alkyl, and wherein no more than 4 of $Y^3$, $Y^4$, $X^2$, $X^3$, and $X^4$ are N;

(c) Substructure D has the following structure,

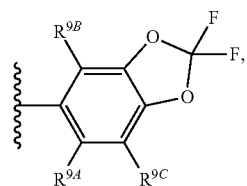

wherein
$R^{9A}$, $R^{9B}$, and $R^{9C}$ are selected, independently, from H, halogen, CN, $C_{1-6}$alkyl, $C_{1-6}$haloalkyl, $C_{1-6}$alkoxy, $C_{1-6}$haloalkoxy, hydroxy$C_{1-6}$ alkyl, or $C_{1-6}$alkoxy-$C_{1-6}$alkyl.

2. The compound of claim 1, wherein
$R^1$ is H, Cl, F, OCH$_3$, OCHF$_2$, or CH$_3$; or
$X^1$ is CH$_2$ or S.

3. The compound of claim 1, wherein $R^5$ is Substructure A.

4. The compound of claim 3, wherein
$R^{6F}$ is H or halogen; or
each of $R^{6A}$, $R^{6B}$, $R^{6C}$, and $R^{6D}$ is H; or
$R^{6A}$ and $R^{6B}$ combine to form =O, or $R^{6C}$ and $R^{6D}$ combine to form =O; or
$R^{6E}$ is $C_{1-6}$ alkyl.

5. The compound of claim 1, wherein $R^5$ is Substructure B.

6. The compound of claim 5, wherein $R^{7A}$ is H or halogen.

7. The compound of claim 1, wherein
n is 2 or 3; or
each $R^{3A}$ and $R^{3B}$ is H.

8. The compound of claim 1, wherein $R^4$ is $NR^{4A}R^{4B}$.

9. The compound of claim 8, wherein $R^{4A}$ is H and $R^{4B}$ is branched $C_{1-6}$ alkyl.

10. The compound of claim 9, wherein —(CR$^{3A}$R$^{3B}$)$_n$R$^4$ is —(CH$_2$)$_2$NHCH$_2$CH(CH$_3$)$_2$.

11. The compound of claim 1, wherein said compound is selected from the group consisting of:

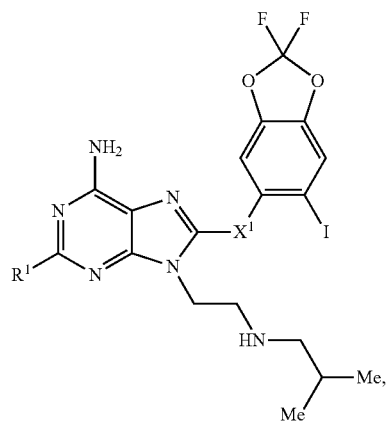

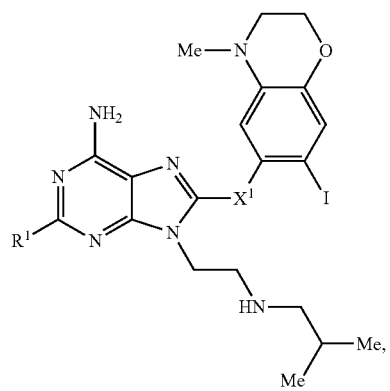

-continued
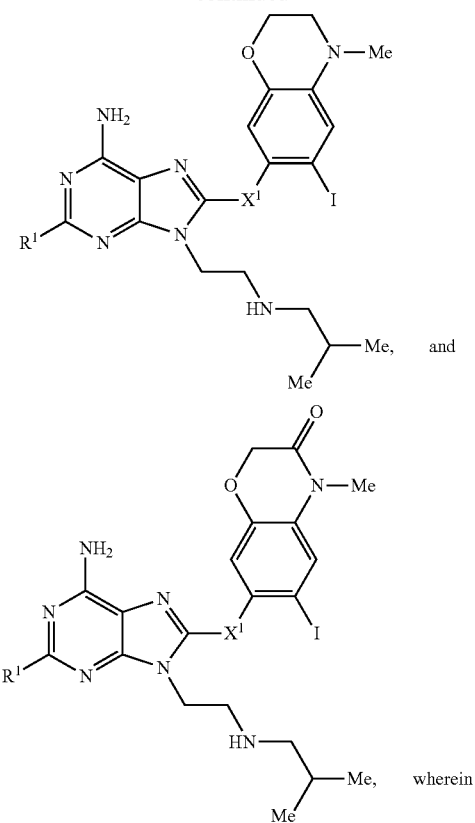
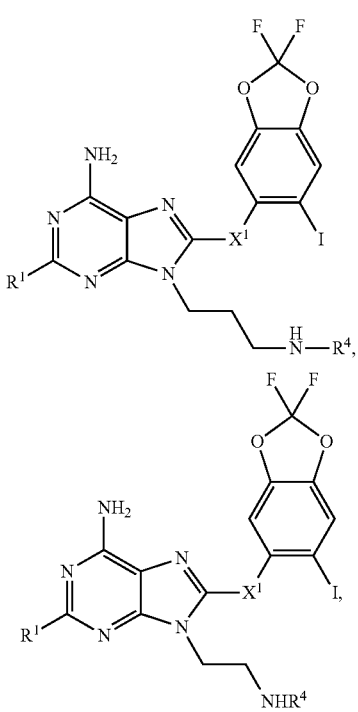
wherein
when $X^1$ is S, $R^1$ is H, and
when $X^1$ is CH$_2$, $R^1$ is F;
and
-continued
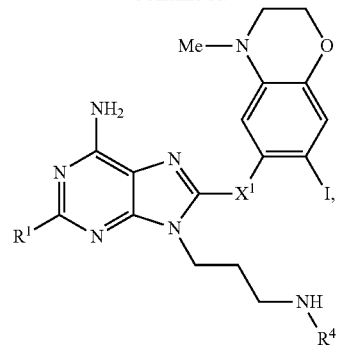
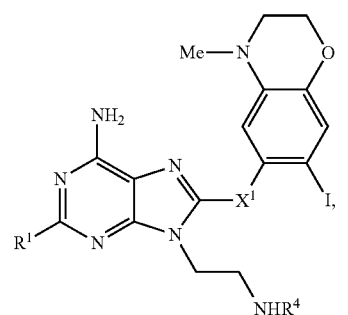
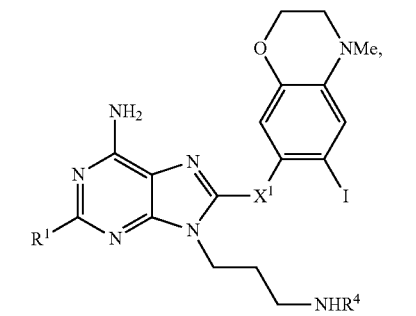
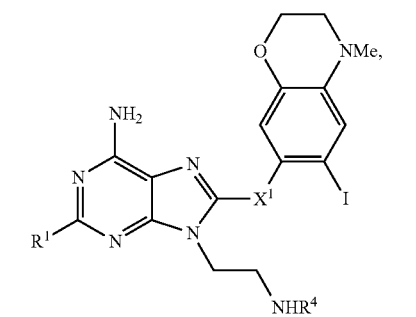
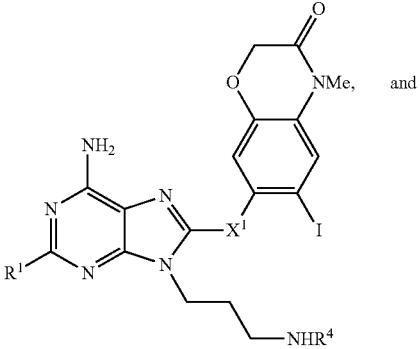

-continued

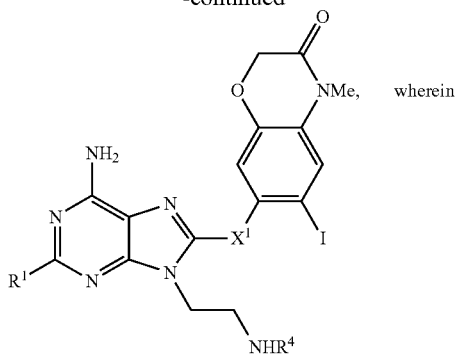

wherein $R^4$ is $C_{1-6}$ alkyl, and
when $X^1$ is S, $R^1$ is H, and
when $X^1$ is $CH_2$, $R^1$ is F.

12. A pharmaceutical composition comprising
 (a) the compound of claim 1, or a tautomer or pharmaceutically acceptable salt, or solvate thereof, and
 (b) a pharmaceutically acceptable excipient.

13. A kit comprising
 (a) the pharmaceutical composition of claim 12; and
 (b) instructions for the use of the pharmaceutical composition of (a) to treat tauopathy, Parkinson's disease, or Huntington's disease in a subject in need thereof.

14. A method of inhibiting heat shock protein 90 (Hsp90) in vitro, said method comprising contacting a cell in vitro with the compound of claim 1, or a tautomer or pharmaceutically acceptable salt, or solvate thereof.

15. A method of treating tauopathy, Parkinson's disease, or Huntington's disease in a subject in need thereof, said method comprising the step of administering the compound of claim 1, or a tautomer or pharmaceutically acceptable salt, or solvate thereof, to said subject in a dosage sufficient to inhibit Hsp90.

* * * * *